(12) United States Patent
Dzija et al.

(10) Patent No.: US 6,656,493 B2
(45) Date of Patent: Dec. 2, 2003

(54) EDIBLE FILM FORMULATIONS CONTAINING MALTODEXTRIN

(75) Inventors: Michael R. Dzija, LaGrange Park, IL (US); David G. Barkalow, Deerfield, IL (US); Albert H. Chapdelaine, Naperville, IL (US); Daniel J. Zyck, North Riverside, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/682,164

(22) Filed: Jul. 30, 2001

(65) Prior Publication Data

US 2003/0035841 A1 Feb. 20, 2003

(51) Int. Cl.$^7$ .................. A61K 47/36; A61K 9/68; A61K 9/28
(52) U.S. Cl. ................ 424/439; 424/440; 424/441
(58) Field of Search ................ 424/439, 440, 424/441

(56) References Cited

U.S. PATENT DOCUMENTS

| | | | |
|---|---|---|---|
| 3,784,390 A | | 1/1974 | Hijiya et al. |
| 4,562,020 A | | 12/1985 | Hijiya et al. |
| 4,777,046 A | * | 10/1988 | Iwakura et al. |
| 4,828,841 A | | 5/1989 | Porter et al. |
| 5,089,307 A | | 2/1992 | Ninomiya et al. |
| 5,286,502 A | | 2/1994 | Meyers |
| 5,376,388 A | | 12/1994 | Meyers |
| 5,409,715 A | | 4/1995 | Meyers |
| 5,433,960 A | * | 7/1995 | Meyers et al. |
| 5,451,673 A | | 9/1995 | Fishman et al. |
| 5,470,581 A | | 11/1995 | Grillo et al. |
| 5,679,389 A | * | 10/1997 | Wong .................. 426/3 |
| 5,948,430 A | * | 9/1999 | Zerbe et al. |

FOREIGN PATENT DOCUMENTS

| | | |
|---|---|---|
| EP | 0 546 538 A1 | 6/1993 |
| EP | 0 547 551 B1 | 6/1993 |
| JP | 5-236885 | 9/1993 |
| WO | WO 00/18365 | 6/2000 |
| WO | WO 00/18835 | 6/2000 |
| WO | WO 00/42992 | 7/2000 |

* cited by examiner

*Primary Examiner*—Carlos Azpuru
(74) *Attorney, Agent, or Firm*—Bell, Boyd & Lloyd LLC

(57) ABSTRACT

Improved edible films for mucoadhesion are provided. The films include at least three types film forming agents other than pullulan, such as maltodextrins, hydrocolloids and fillers. Medicaments and other additive agents can also be incorporated into the edible films. In this regard, the edible films can be utilized to deliver or release the medicaments into an oral cavity, thereby providing effective oral treatment with respect to, for example, oral cleansing and breath freshening.

20 Claims, No Drawings

EDIBLE FILM FORMULATIONS CONTAINING MALTODEXTRIN

BACKGROUND OF THE INVENTION

The present invention generally relates to edible compositions. More specifically, the present invention relates to edible film formulations.

Of course, oral cleansing and breath freshening are an important part of everyday life. In order to facilitate proper oral hygiene, oral cleansing and breath freshening practices should be conducted repeatedly throughout the day.

However, oral cleansing and breath freshening may be difficult or inconvenient at times, depending on the nature of the breath freshening desired and the situation in which the breath freshening must occur. Brushing, flossing, cleaning your tongue and gargling using a variety of devices and compositions are common oral care practices well-suited for the privacy of one's home. But, such devices and compositions are less convenient to use away from the home where bathroom facilities might be scarce, unavailable or unsanitary.

To deal with this issue, less obtrusive oral products have been developed. These include breath-freshening gums, lozenges, mouth sprays and edible films.

A number of different edible film compositions are currently available for consumption. Many of the products use pullulan. However, pullulan is an expensive ingredient and may have limited availability. Other edible materials have been employed as a substitute for pullulan within edible film compositions. These materials include modified starches and cellulosics. Unfortunately, such materials typically lack one or more of pullulan's desirable film properties. These properties include, for example, rapid dissolution, clean mouth feel, clean flavor and ease of manufacture.

A need, therefore exists, for improved edible film formulations that exhibit the desirable film properties that are exhibited by pullulan-based edible films.

SUMMARY OF THE INVENTION

The present invention provides improved edible film formulations and methods of making and using same. The edible films include at least three types of film forming agents other than pullulan that are readily available and can be made at lower costs. In this regard, the mixture of film forming agents, such as maltodextrins, hyrdrocolloids and fillers, can be used to prepare "stand alone" films that can provide oral cleansing and breath freshening effects while displaying clean flavor and mouth feel, rapid dissolution and ease of manufacture. Medicaments and other additive agents can also be incorporated into the edible films thereby providing effective oral treatment, such as oral cleansing and breath freshening.

To this end, in an embodiment of the present invention, a stand alone edible film for oral mucoadhesion is provided. The stand alone edible film includes at least three types of film forming agents and not including pullulan.

In an embodiment, the film forming agents include a maltodextrin, a hydrocolloid and a filler.

In another embodiment of the present invention, an edible film is provided including a maltodextrin, a hydrocolloid and a bulk filler and not including a pullulan.

In yet another embodiment, a method of producing an edible film for oral mucoadhesion is provided. The method includes the steps of preparing a base solution including at least three types of film forming agents other than pullulan and processing the base solution to form the edible film.

In still yet another embodiment, a method of oral treatment is provided. The method includes the steps of providing a food-grade film including at least three types of film forming agents and a medicament; orally consuming the food-grade film and releasing the medicament in an oral cavity.

It is, therefore, an advantage of the present invention to provide edible films for mucoadhesion that include at least three types of film forming agents other than pullulan.

Another advantage of the present invention is to provide edible films that include a medicament for cleansing an oral cavity and freshening breath upon consumption.

A further advantage of the present invention is to provide a method for delivering the medicament into an oral cavity for treating same.

Yet a still further advantage of the present invention is to provide a method for oral treatment that utilizes edible film formulations which can effectively release a medicament in the oral cavity upon consumption.

Moreover, an advantage of the present invention is to provide a stand alone film.

Additional features and advantages of the present invention are described in, and will be apparent in, the detailed description of the presently preferred embodiments.

DETAILED DESCRIPTION OF THE INVENTION

The present invention provides edible film formulations for oral mucoadhesion and methods of using and making same. In particular, the edible films of the present invention include at least three types of film forming agents other than pullulan.

Applicants have uniquely discovered that the use of a mixture of at least three types of film forming agents, such as maltodextrins, fillers (e.g., microcrystalline cellulose (MCC)) and hydrocolloids (e.g.,sodium alginate), can be effectively utilized to prepare "stand alone" edible films. The edible films are composed of ingredients that are readily available, can be prepared at lower costs and display similar properties as compared to edible films composed of pullulan. In this regard, the edible films can provide a physiologically acceptable film, which is suitably adapted to adhere to oral surfaces of an oral cavity and rapidly dissolve therein.

The edible films of the present invention can be utilized to deliver or release oral care agent(s). Such agents include, anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

In an embodiment, the edible or food-grade film of the present invention includes at least three types of film forming agents other than pullulan. The edible films can also include a medicament for oral cleansing and/or breath freshening. Further, the edible films can include a variety of other suitable ingredients, such as softeners, colorants, flavoring agents, emulsifiers, surfactants, thickening agents, binding agents, sweeteners, fragrances, other like ingredients or combinations thereof.

In an embodiment, the edible films preferably include a mixture of at least three types of film forming agents, such as maltodextrins, fillers and hydrocolloids. It should be appreciated that the edible film of the present invention can be composed of one or more different compounds associated with each of the at least three types of film forming agents.

In an embodiment, the maltodextrin component constitutes between about 5% to about 60% by dry weight of the edible film, preferably about 20% to about 40% by dry weight. The maltodextrin component can be processed in any suitable way.

The hydrocolloid can provide thickness and decrease brittleness of the edible films. The hydrocolloid can include any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

Any suitable food-grade bulk filler can also be added to the edible film. This can reduce any "slimy" texture as well as provide structure to the film thereby making it more palatable. In an embodiment, the filler can constitute about 5% to about 30% by dry weight of the film, preferably about 15% to about 25% by dry weight. The filler can include, for example, microcrystalline cellulose, cellulose polymers, such as wood, magnesium and calcium carbonate, ground limestone, silicates, such as magnesium and aluminum silicate, clay, talc, titanium dioxide, mono-calcium phosphate, di-calcium phosphate, tri-calcium phosphate, other like bulk fillers or combinations thereof.

It is believed that the unique mixture of at least three film forming agents other than pullulan, for example, a maltodextrin, a hydrocolloid and a bulk filler, can provide a "stand alone" edible film composition which exhibits many of the same desirable properties exhibited by the more expensive pullulan-based edible film. Applicants have desirably discovered that the pullulan-free edible film formulation of the present invention can exhibit, for example, clean mouth feel, clean favor and ease of manufacture similar to currently available pullulan-based films.

As previously discussed, a variety of other suitable ingredients can be added to the edible film of the present invention. For example, any suitable medicament for oral cleansing, breath freshening or the like can be added to the film formulation. The medicaments can include, for example, a pH control agent, such as urea and buffers, inorganic components for tartar or caries control, such as phosphates and fluorides, a breath freshening agent, such as zinc gluconate, an anti-plaque/anti-gingivitis agent, such as chlorohexidene, CPC, and triclosan, a saliva stimulating agent including, for example, food acids such as citric, lactic, maleic, succinic, ascorbic, adipic, fumaric and tartaric acids, a pharmaceutical agent, a nutraceutical agent, a vitamin, a mineral, other like medicaments or combinations thereof.

The medicaments can be delivered or released into the oral cavity for effective oral treatment, such as oral cleansing and/or breath freshening. In this regard, the film forming agents of the edible film can act to entrap the medicaments within the oral cavity thereby providing extended efficacy thereof. In doing so, it is believed that the pullulan free edible film compositions of the present invention more uniformly release the medicament into the oral cavity for absorption via open wounds or mucous membrane in a greater manner than could be previously achieved. Moreover, it is also believed that the mixture of film-forming agents of the present invention can entrap the medicament within the oral cavity for an extended period of time to prolong and enhance the effects of the medicament. In addition, by extending the contact time of the medicament within the oral cavity, the medicament is absorbed to a greater extent thereby increasing its bioavailability.

If reduced levels of film forming agents are utilized, softeners can be used to reduce the brittleness of the resulting films. The softeners, which are also known as plasticizers or plasticizing agents, generally constitute between about 0% to about 20% by dry weight of the film, preferably about 2% to about 10% by dry weight. The softeners can include plasticizers containing, for example, sorbitol and other polyols, glycerin, polyethylene glycol, propylene glycol, hydrogenated starch hydrolysates, corn syrups, other like material or combinations thereof.

The edible film formulations of the present invention can also include colorants or coloring agents which can be used in any suitable amount to produce the desired color. Coloring agents can include, for example, natural food colors and dyes suitable for food, drug and cosmetic applications. The colorants are typically known as FD&C dyes and lakes.

A variety of flavoring agents can also be added to the edible films. Any suitable amount and type of artificial and/or natural flavoring agents can be used in any sensorially acceptable fashion. For example, the flavor can constitute about 0.1% to about 20% by dry weight of the film, preferably about 10% to 15%. The flavoring agent can include, for example, essential oils, synthetic flavors or mixtures including but not limited to oils derived from plants and fruits such as citrus oil, fruit essences, peppermint oil, spearmint oil, other mint oils, clove oils, oil of wintergreen, anise and the like, flavor oils with germ killing properties such as menthol, eucalyptol, eugenol, thymol, like flavoring agents or combinations thereof.

The flavor can be enhanced and evenly distributed throughout the product by emulsification. Any suitable amount and type of natural and/or synthetic food-grade emulsifier can be used. For example, the emulsifier can include lecithin, food-grade non-ionic emulsifiers, such as fatty acids ($C_{10}$–$C_{18}$) mono and diacyl glycerides, ox bile extract, polyglycerol esters, polyethylene sorbitan esters, propolyene glycol, sorbitan monopalmitate, sorbitan monosterate, sorbitan tristerate, other like emulsifiers or combinations thereof.

The flavors can be emulsified by any suitable emulsification process, such as mechanical processing, vigorous stirring, intense pressure fluctuations that occur in turbulent flow such as homogenization, sonication, colloid milling and the like.

The present invention provides methods of producing the edible film formulations. In general, the edible film formulations are prepared by forming a base solution that includes at least three types of film forming agents, such as maltodextrins, hydrocolloids and fillers and processing the base solution to form an edible film. Typically, the base solution is prepared by adding an initial mixture of dry ingredients to water that is stirred.

To the base solution, additional ingredients, such as flavor/emulsifier blends, sweeteners, softeners, color, the like or combinations thereof, can be added. In an embodiment, the solution is stirred continuously and heated at a temperature ranging from about 40° C. to about 50° C. The solution then can be dried in any suitable manner, thereby, forming the edible film.

It should be appreciated that any suitable type, number and arrangement of process procedures or steps (i.e., mixing, heating, drying, cooling, addition of ingredients), process parameters (i.e., temperature, pressure, pH, process times) or the like can be utilized.

By way of example and not limitation, the following examples illustrate various embodiments of the edible film formulations of the present invention.

EXAMPLES (% dry weight)

PREPARATION OF EXAMPLES 1–5

Examples 1–5 were prepared by making edible films from maltodextrin. A mixture of dry ingredients, such as maltodextrin, sodium alginate and microcrystalline cellulose, was slowly added to water while stirring. The solution was continually stirred and heated to boiling. After which, it was removed from the heat and cooled to a temperature of about 35° C. to about 40° C. The other ingredients, such as flavor/emulsifier blends, sweeteners, softeners and color, were added to the solution while stirring and at a temperature of about 35° C. to about 40° C. The solution was spread onto a glass plate by utilizing a draw down blade. A film was formed on the glass plate by drying the solution in an oven for about 15 minutes at 40° C. After which, the film was removed from the plate and cut into desired pieces.

The edible films of Examples 1–5 were compared for sensory analysis. All of the films exhibited differences in texture and mouth feel. Example 1 provided good mouth feel, clean flavor, fast dissolution and flexibility. In comparison, Example 2 had good flexibility, but was found

| Ingredient | Example 1 | Example 2 | Example 3 | Example 4 | Example 5 |
|---|---|---|---|---|---|
| Maltodextrin | 36.00 | 32.45 | 31.15 | 30.00 | 37.00 |
| Sodium Alginate | 22.15 | 20.00 | 19.00 | 31.15 | — |
| Carageenan | — | — | — | — | 23.15 |
| Microcrystalline Cellulose | 20.00 | 18.00 | 17.00 | 17.00 | 18.00 |
| Gum Arabic | — | — | 11.00 | — | — |
| Glycerin | 7.30 | 15.00 | 7.30 | 7.30 | 7.30 |
| Flavor | 11.00 | 11.00 | 11.00 | 11.00 | 11.00 |
| Lecithin | 2.00 | 2.00 | 2.00 | 2.00 | 2.00 |
| High Intensity Sweetener | 1.50 | 1.50 | 1.50 | 1.50 | 1.50 |
| Color | 0.05 | 0.05 | 0.05 | 0.05 | 0.05 |
| | 100.00 | 100.00 | 100.00 | 100.00 | 100.00 |

| Ingredient | Example 6 | Example 7 | Example 8 | Example 9 | Example 10 |
|---|---|---|---|---|---|
| Maltodextrin | 25.95 | 50.00 | 35.00 | 43.00 | 26.00 |
| Sodium Alginate | 22.50 | — | 19.00 | — | 12.00 |
| Calcium Alginate | — | 5.15 | — | 13.25 | — |
| Carageenan | — | — | — | — | 12.00 |
| Microcrystalline Cellulose | 25.75 | 9.00 | 20.00 | 13.00 | 25.00 |
| Calcium Carbonate | — | 2.45 | — | — | — |
| Glycerin | 12.25 | 10.00 | 8.00 | — | 9.5 |
| Sorbitol | — | — | — | 6.00 | 1.55 |
| Popylene Glycol | — | — | 3.65 | 5.00 | — |
| Menthol | 1.00 | 0.05 | — | 1.25 | — |
| Eucalyptol | — | 0.05 | — | 1.00 | — |
| Maleic Acid | — | — | — | — | 1.35 |
| Citric Acid | — | — | 1.25 | — | 1.00 |
| Chlorohexidene | 1.85 | — | — | 1.00 | — |
| Triclosan | — | 1.25 | — | 1.00 | — |
| Flavor | 9.40 | 11.00 | 12.00 | 14.00 | 10.00 |
| High Intensity Sweetener | 1.25 | 1.00 | 1.05 | 1.45 | 1.50 |
| Color | 0.05 | 0.05 | 0.05 | 0.05 | 0.10 |
| | 100.00 | 100.00 | 100.00 | 100.00 | 100.00 | to be too sticky to handle. In Example 3, the addition of gum arabic showed no improvement in flexibility. Example 4 was slightly slimy and showed no improvement in flexibility. Example 5 was slimy, slow to dissolve, yet sufficiently flexible.

It should be understood that various changes and modifications of the presently preferred embodiments described herein will be apparent to those skilled in the art. Such changes and modifications can be made without departing from the spirit and scope of the present invention and without diminishing its intended advantages. It is therefore intended that all such changes and modifications be covered by the appended claims.

What is claimed is:

1. A stand alone edible film for oral mucoadhesion comprising at least three types of film forming agents and not including pullulan wherein the film forming agents comprise a maltodextrin, a hydrocolloid and a filler.

2. The stand alone edible film of claim 1 wherein the film forming agents comprise a maltodextrin, a hydrocolloid and a filler.

3. A stand alone edible film for oral mucoadhesion comprising at least three types of film forming agents and not including pullulan wherein the film forming agents comprise a maltodextrin, a hydrocolloid and a filler, and the maltodextrin comprises about 5% to about 60% by dry weight of the stand alone edible film.

4. A stand alone edible film for oral mucoadhesion comprising at least three types of film forming agents and not including pullulan wherein the film forming agents comprise a maltodextrin, a hydrocolloid and a filler, and the filler comprises about 5% to about 30% by dry weight of the stand alone edible film.

5. The stand alone edible film of claim 4 wherein the filler is selected from the group consisting of microcrystalline cellulose, cellulose polymers, magnesium and calcium carbonate, ground limestone, silicates including magnesium and aluminum silicate, clay, talc, titanium dioxide, monocalcium phosphate, di-calcium phosphate, tri-calcium phosphate and combinations thereof.

6. A stand alone edible film for oral mucoadhesion comprising at least three types of film forming agents and not including pullulan wherein the film forming agents comprise a maltodextrin, a hydrocolloid and a filler, and the hydrocolloid further comprises about 10% to about 50% by dry weight of the stand alone edible film.

7. The stand alone edible film of claim 6 wherein the hydrocolloid is selected from the group consisting of natural seaweeds, natural seed gums, natural plant exudates, natural fiber extracts, biosynthetic gums, gelatins, biosynthetic processed starch or cellulosic materials, alginates, sodium alginate, calcium alginate, carrageenan, guar gum, locust gum, tara gum, gum arabic, ghatti gum, agar gum, xanthan gum, pectin and combinations thereof.

8. The stand alone edible film of claim 1 wherein the stand alone edible film includes a medicament.

9. The stand alone edible film of claim 8 wherein the medicament is selected from the group consisting of a pH control agent, an oral care agent, a breath freshening agent, a pharmaceutical agent, a nutraceutical agent, a salivary stimulant agent, a vitamin, a mineral, an anti-microbial agent, an anti-plaque agent, an anti-gingivitis agent, a tartar or caries control agent and combinations thereof.

10. An edible film comprising a maltodextrin, a hydrocolloid and a bulk filler and not including a pullulan.

11. The edible film of claim 10 wherein the maltodextrin constitutes about 20% to about 40% by dry weight of the edible film.

12. The stand alone edible film of claim 10 wherein the hydrocolloid constitutes about 20% to about 30% by dry weight of the edible film.

13. The stand alone edible film of claim 10 wherein the bulk filler comprises about 15% to about 25% by dry weight of the edible film.

14. A method of producing an edible film for oral mucoadhesion comprising the steps of:

preparing a base solution including at least three types of film forming agents other than pullulan wherein the film forming agents comprise a maltodextrin, a hydrocolloid and a filler; and processing the base solution to form the edible film.

15. A method of producing an edible film for oral mucoadhesion comprising the steps of:

preparing a base solution including at least three types of film forming agents other than pullulan; and processing the base solution to form the edible film, wherein the film forming agents comprise a maltodextrin ranging from about 5% to about 60% by dry weight of the edible film, a hydrocolloid ranging from about 10% to about 50% by dry weight of the edible film and a filler ranging from about 5% to about 30% by dry weight of the edible film.

16. The method of claim 14 wherein the base solution is processed by adding a therapeutically effective amount of a medicament selected from the group consisting of a pH control agent, an oral care agent, a breath freshening agent, a pharmaceutical agent, a nutraceutical agent, a salivary stimulant agent, a vitamin, a mineral, an anti-microbial agent, an anti-plaque agent, an anti-gingivitis agent, a tartar or caries control agent and combinations thereof.

17. A method of oral treatment comprising the steps of:

providing a food-grade film including at least three types of film forming agents other than pullulan wherein the film forming agents comprise a maltodextrin, a hydrocolloid, a filler and a medicament;

orally consuming the food-grade film; and releasing the medicament in an oral cavity.

18. A method of oral treatment comprising the steps of:

providing a food-grade film including at least three types of film forming agents and a medicament;

orally consuming the food-grade film; and releasing the medicament in an oral cavity, wherein the film forming agents comprise a maltodextrin ranging from 5% to about 60% by dry weight of the edible film, a hydrocolloid ranging from about 10% to about 50% by dry weight of the edible film and a filler ranging from about 5% to about 30% by dry weight of the edible film.

19. The method of claim 17, wherein the medicament is selected from the group consisting of a pH control agent, an oral care agent, a breath freshening agent, a pharmaceutical agent, a nutraceutical agent, a salivary stimulant agent, a vitamin, a mineral, an anti-microbial agent, an anti-plaque agent, an anti-gingivitis agent, a tartar or caries control agent or combinations thereof.

20. The method of claim 17, wherein the medicament is released in the oral cavity to treat halitosis, dental plaque, gingivitis, xerostomia, dry mouth, oral malodor or combinations thereof.

* * * * *